United States Patent [19]

Haskvitz et al.

[11] Patent Number: 5,273,537
[45] Date of Patent: Dec. 28, 1993

[54] POWER-ASSISTED INFLATION APPARATUS

[75] Inventors: David J. Haskvitz, Golden Valley; John W. Humphrey, Eden Prairie; William F. Kratoska, Plymouth; Richard R. Prather, Richfield; David J. Serdar, Shorewood, all of Minn.

[73] Assignee: SciMed Life Systems, Inc., Maple Grove, Minn.

[21] Appl. No.: 847,826
[22] Filed: Mar. 6, 1992
[51] Int. Cl.⁵ .................. A61M 29/00; A61M 37/00
[52] U.S. Cl. ........................ 604/99; 604/155
[58] Field of Search ............... 604/96-100, 604/118, 121, 151-155, 65, 67; 128/DIG. 12, DIG. 13

[56] References Cited

U.S. PATENT DOCUMENTS

| | | | |
|---|---|---|---|
| 3,155,090 | 11/1964 | Holter | 128/2 |
| 3,425,416 | 2/1969 | Loughry | 604/155 |
| 3,631,847 | 1/1972 | Hobbs, II . | |
| 3,701,345 | 10/1972 | Heilman et al. | 604/121 X |
| 3,720,199 | 3/1973 | Rishton et al. . | |
| 3,858,581 | 1/1975 | Kamen . | |
| 3,945,379 | 3/1976 | Pritz et al. . | |
| 4,036,232 | 7/1977 | Genese . | |
| 4,180,067 | 12/1979 | Derlien . | |
| 4,191,187 | 3/1980 | Wright | 604/155 |
| 4,269,185 | 5/1981 | Whitney et al. . | |
| 4,285,340 | 8/1981 | Gezari et al. . | |
| 4,331,156 | 5/1982 | Apple et al. . | |
| 4,332,254 | 6/1982 | Lundquist . | |
| 4,407,659 | 10/1983 | Adam | 604/155 |
| 4,409,986 | 10/1983 | Apple et al. . | |
| 4,435,173 | 3/1984 | Siposs et al. | 609/155 |
| 4,439,185 | 3/1984 | Lundquist | 604/97 |
| 4,439,186 | 3/1984 | Kuhl | 604/99 |
| 4,508,532 | 4/1985 | Drews et al. | 604/22 |
| 4,525,156 | 7/1985 | Benusa et al. | 604/28 |
| 4,529,397 | 7/1985 | Hennemuth et al. | 604/4 |
| 4,529,401 | 7/1985 | Leslie et al. | 604/131 |
| 4,560,979 | 12/1985 | Rosskopf | 340/540 |
| 4,573,992 | 3/1986 | Marx | 604/408 |
| 4,585,439 | 4/1986 | Michel | 604/155 |
| 4,613,327 | 9/1986 | Tegrarian et al. | 604/141 |
| 4,627,835 | 12/1986 | Fenton, Jr. | 604/67 |
| 4,666,430 | 5/1987 | Brown et al. | 604/141 |
| 4,668,220 | 5/1987 | Hawrylenko | 604/155 |
| 4,697,574 | 10/1987 | Karcher et al. . | |
| 4,731,058 | 3/1988 | Doan | 604/155 |
| 4,767,406 | 8/1988 | Wadham et al. | 604/155 |
| 4,804,368 | 2/1989 | Skakoon et al. | 604/155 |
| 4,887,608 | 12/1989 | Mohl et al. . | |
| 4,909,783 | 3/1990 | Morrison | 604/30 |
| 4,934,996 | 6/1990 | Mohl et al. . | |
| 4,944,726 | 7/1990 | Hilal et al. | 604/143 |
| 4,969,470 | 11/1990 | Mohl et al. . | |
| 4,978,335 | 12/1990 | Arthur, III | 604/67 |
| 5,004,472 | 4/1991 | Wallace | 606/194 |
| 5,006,112 | 4/1991 | Metzner | 604/155 |
| 5,009,662 | 4/1991 | Wallace et al. | 606/192 |
| 5,015,223 | 5/1991 | McGough et al. | 604/97 |
| 5,019,037 | 5/1991 | Wang et al. | 604/32 |
| 5,021,046 | 6/1991 | Wallace | 604/97 |
| 5,034,003 | 7/1991 | Denance | 604/117 |
| 5,047,012 | 9/1991 | Leuschner et al. | 604/32 |
| 5,090,963 | 2/1992 | Gross et al. | 604/132 |
| 5,135,488 | 8/1992 | Foote et al. | 604/97 |
| 5,152,776 | 10/1992 | Pinchuk | 606/192 |
| 5,171,299 | 12/1992 | Heitzmann et al. | 604/100 |

FOREIGN PATENT DOCUMENTS

1909540  9/1970  Fed. Rep. of Germany ........ 604/155

Primary Examiner—John D. Yasko
Assistant Examiner—Adam J. Cermak
Attorney, Agent, or Firm—Kinney & Lange

[57] ASBSTRACT

Inflation apparatus for inflating a dilatation balloon of a catheter includes a frame having a first receiver supporting the barrel of a syringe. An operator has a second receiver supporting the plunger of the syringe. The syringe includes a fluid port for connecting the syringe chamber to the lumen of the catheter. A motor is supported by the frame and operatively connected to the operator to move the piston to change fluid pressure within the syringe chamber. A release device permits quick release of the pressure in the balloon catheter without the use of the motor. A pressure sensor is mounted to the frame to measure the pressure in the chamber through a diaphragm on the syringe. The pressure sensor operates a microprocessor-controlled display, which provides display of inflation and duration information and calculates other information. A circuit selectively operates the motor. An inflation control connected to the circuit permits operation of the motor at selected rates of inflation/deflation or to selected specific inflation pressures.

23 Claims, 6 Drawing Sheets

POWER-ASSISTED INFLATION APPARATUS

This invention relates to an inflation apparatus for inflating dilatation balloons used in angioplasty procedures, and particularly to inflation apparatus employing power-assisted pressure applicators.

BACKGROUND OF THE INVENTION

Angioplasty procedures are accepted to dilatate stenoses or blockages within a human body. Examples of such procedures include percutaneous transluminal coronary angioplasty (PTCA) procedures and urological procedures. The present invention will be described with application to PTCA procedures, although the invention is equally applicable to other PTA procedures. The PTCA procedure employs a percutaneous intrusion into the arterial system and advancement of a dilatation balloon catheter to the location of the stenosis. The dilatation balloon is positioned across the stenosis, and the balloon is inflated through use of an inflation device connected to the catheter and in fluid communication with the balloon through a lumen in the catheter.

Most inflation devices currently in use are hand operated. Inflation devices include a syringe having a chamber in fluid communication with the lumen of the catheter, and a piston within the chamber connected to a plunger operable by the cardiologist to increase the pressure of inflation fluid within the chamber. The pressure applied to the balloon may be as great as 15 atmospheres or more, during a typical PTCA procedure. It is not unusual to inflate the balloon to pressures as high as 200 to 250 pounds per square inch.

A typical PTCA procedure requires use of at least an introducer, a guide catheter, and a balloon catheter. The introducer provides percutaneous intrusion through the skin into the arterial system, the guide catheter provides a guide for delivery of the balloon catheter and other items within the arterial system, and the dilatation balloon catheter is advanced within the guide catheter to the stenosis where the balloon is positioned to dilatate the same. A guidewire is often also used to guide the guide catheter and/or the balloon catheter during their respective advancements. Typically, the components are advanced until each component is at the position desired by the cardiologist, whereupon each component is held in a fixed position relative to the other elements, and relative to the stenosis. With the position of each component fixed, the inflation device is attached to the proximal end of the balloon catheter and pressure is applied thereto. Typically, the procedure requires at least two people, and sometimes more, one to hold the position of the components and another to operate the inflation device. It has not been possible for one person to easily and accurately simultaneously maintain component position and operate the manually-operated inflation device.

Power-assisted inflation apparatus have been proposed, but they have not been entirely satisfactory to cardiologists. As an example, it is important that the components used in the PTCA procedure, including the inflation device, be sterile. Manually-operated inflation devices are reasonably economic that they may be discarded after each procedure rather than sterilized. However, most proposed power-assisted inflation devices would be so costly to manufacture that it would not be economically feasible to discard them after each use. Sterilization of such devices after use would also be expensive. Moreover, the PTCA procedure performed with most proposed power-assisted inflation devices would still require two or more persons, so such proposed power-assisted inflation devices would not meet the needs of the users. Further, many proposed power-assisted inflation devices would not provide accurate control over pressure applied to the dilatation balloon. Consequently, power-assisted inflation devices have not been accepted by the users.

There is a need, therefore, for a power-assisted inflation apparatus which may be operated with one hand so that the cardiologist may use the other hand for other purposes (including maintaining the position of the catheter components), and which is economically returnable to a sterile state after use, and which provides easy, accurate control over pressure within the dilatation balloon.

SUMMARY OF THE INVENTION

The present invention relates to an inflation apparatus for inflating a dilatation balloon of a catheter having a lumen in fluid communication with the dilatation balloon during an angioplasty procedure. The apparatus includes a frame having a first receiver supporting the barrel of a syringe, and an operator having a second receiver supporting the piston of the syringe. The syringe includes a connector for connecting the syringe chamber to fluid communication with the lumen of the catheter. A motor is supported by the frame and operatively connected to the operator to move the piston to change fluid pressure within the syringe chamber. A circuit selectively operates the motor.

In a preferred form of the invention, a pressure sensor is mounted to the frame and arranged to measure the pressure in the chamber of the syringe. The pressure sensor provides an electric signal representative of fluid pressure within the chamber, and display means is responsive to the electric signal to display data.

One feature of the invention resides in the use of a disposable syringe, the syringe barrel being closed with a diaphragm to transmit pressure to the pressure sensor.

Another feature of the invention resides in the inclusion of a release mechanism to permit release of pressure in the syringe and balloon catheter without operation of the motor.

Another feature of the invention resides in the provision of a microprocessor to receive signals from the pressure sensor to provide display and/or recordation of inflation and duration information and to calculate other information relating to the procedure.

Another feature of the invention resides in the use of the microprocessor to control the inflation/deflation procedure, either under program control or through inflation controls operable by the cardiologist, the microprocessor providing control for the motor.

Another feature of the present invention resides in the provision of inflation controls permitting the cardiologist to select inflation pressures or rates of inflation.

DETAILED DESCRIPTION OF THE PREFERRED EMBODIMENTS

Figure 1:
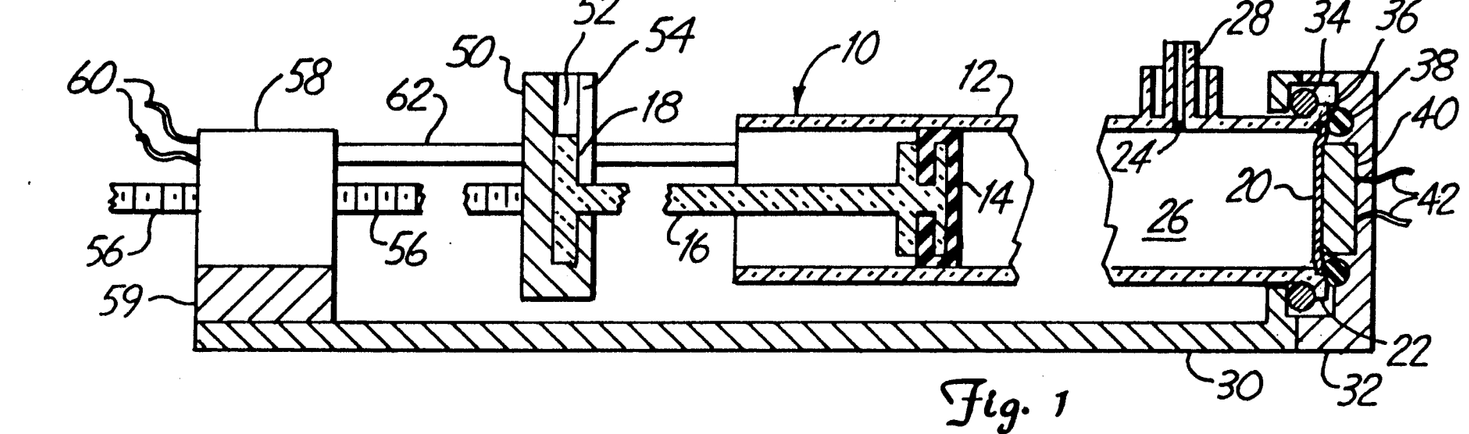
FIG. 1 is a side view, partly in cutaway cross-section, of an inflation apparatus according to one embodiment of the present invention.
Figure 2:
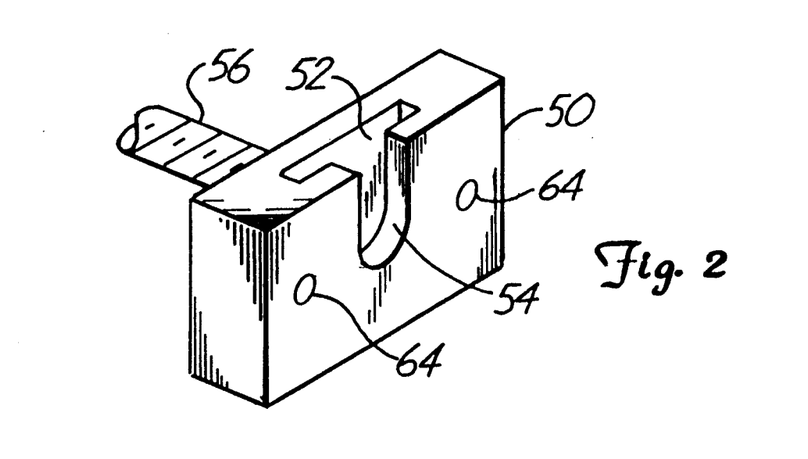
FIG. 2 is a perspective view of an operator mechanism for operating the plunger of the inflation apparatus illustrated in FIG. 1.

FIGS. 1 and 2 illustrate an inflation apparatus in accordance with one embodiment of the present invention. The inflation apparatus includes a disposable syringe 10 having a barrel 12 containing piston 14 connected to one end of plunger 16. Plunger actuator 18 is connected to the other end of plunger 16 and is operable to move the plunger, and hence piston 14, axially within barrel 12. One end of barrel 12 is closed by stainless diaphragm 20. That same end also includes an external lip 22. Port 24 provides fluid communication between the internal chamber 26 of syringe 10 and the lumen of a balloon catheter (not shown) whose proximal end is connected to connector 28, in fluid communication with port 24.

Disposable syringe 10 is placed within a housing having a frame 30 to which is attached cap 32. Detents 34 bear against lip 22 of barrel 12 so that forward face 36 of barrel 12 bears against O-ring 38 attached to cap 32. Pressure sensor 40 is mounted in cap 32 and includes a sensor surface which extends beyond the plane of O-ring 38 to bear tightly against diaphragm 20. Sensor 40 provides an electric signal on leads 42, to be described below.

Plunger operator 50 includes a receiver comprising a first slot 52 sized to receive plunger actuator 18, and a second smaller slot 54 through which plunger 16 extends. Operator 50 is connected to the shaft 56 of motor 58 which in turn is mounted to frame 30. In one form of the invention, motor 58 is mounted to release mechanism 59 which in turn is releasably mounted to frame 30. Release mechanism 59, which may contain compression springs and the like, is arranged to be manually disconnected (such as by a button similar to button 104 described below) from frame 30 to bias motor 58 to the left (in the illustration of FIG. 1), to force plunger 1b to the left (in the illustration of FIG. 1) to thereby rapidly and mechanically create a vacuum in chamber 26 to deflate the dilatation balloon attached to the catheter. Motor 58 is electrically operated via leads 60 to axially move shaft 56. If desired, support rods 62 may be mounted to the ends of frame 30 and pass through apertures 64 of operator 52 to provide additional support therefore.

In use, disposable syringe 10 is mounted to frame 30 by snapping the distal end of barrel 12 into cap 32 so that detents 34 bear against lip 22 to hold the barrel to the cap. When so positioned, diaphragm 20 mates snugly against pressure sensor 40 so that pressure in chamber 26 is transferred to sensor 40. Actuator 18 is received in slot 52 of operator 50. When in the assembled position shown in FIG. 1, syringe 10 is axially aligned with motor 58 and its shaft 56. Chamber 26 of syringe 10 may be preloaded with a suitable inflation fluid prior to mounting the syringe into frame 30. Alternatively, chamber 26 may be automatically loaded with an inflation fluid after the syringe has been mounted to the frame through connection to a fluid supply and operating plunger 16 through microprocessor 120 and motor 58 to draw fluid into the chamber. Typically, the inflation fluid is a sterile saline and radiopaque mixture. The proximal end of a balloon catheter (not shown) is connected through a manifold and tube (not shown in FIG. 1) to connector 28 in fluid communication with chamber 26. Motor 58 is electrically energized to move operator 50 and plunger 16 to cause piston 14 to move axially in barrel 12 to change the pressure of the fluid in chamber 26. The pressure within chamber 26 is transmitted through the lumen of the catheter to the dilatation balloon, and is transmitted through diaphragm 20 to pressure sensor 40 to provide a signal output indicative of the pressure within the distal dilatation balloon.

Figure 3:
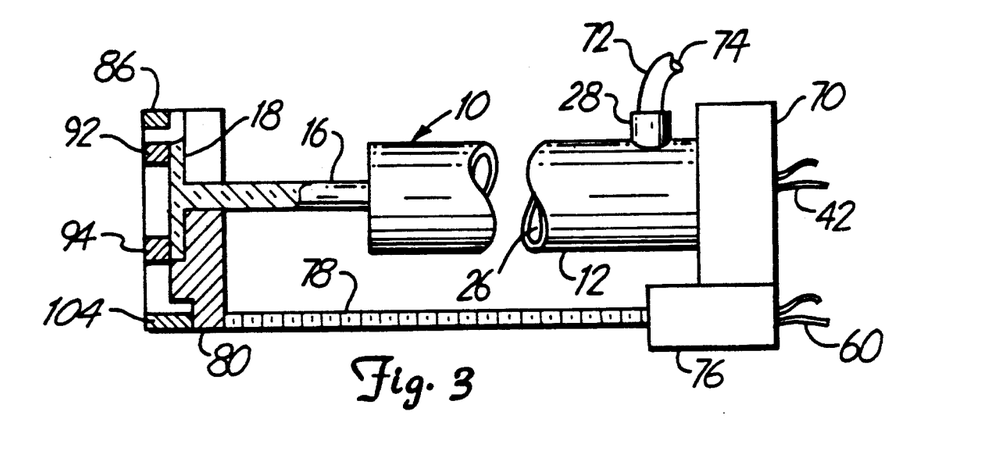
FIG. 3 is a side view, partly in cutaway cross-section, of an inflation apparatus in accordance with the presently preferred embodiment of the present invention.
Figure 4:
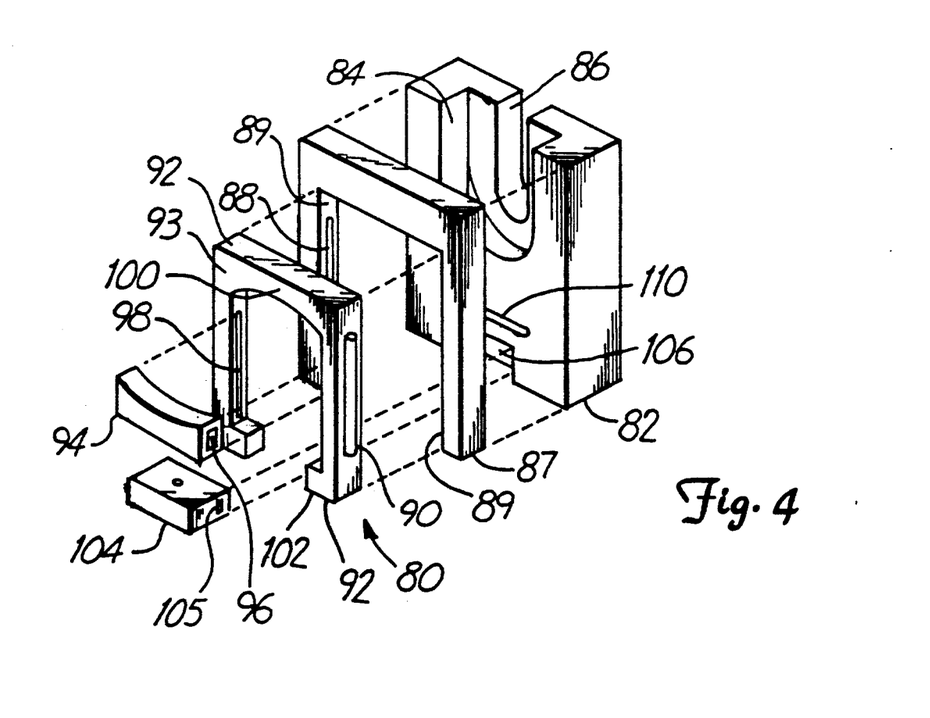
FIGS. 4 and 5 illustrate the operator mechanism for operating the plunger of the inflation apparatus illustrated in FIG. 3.
Figure 5:
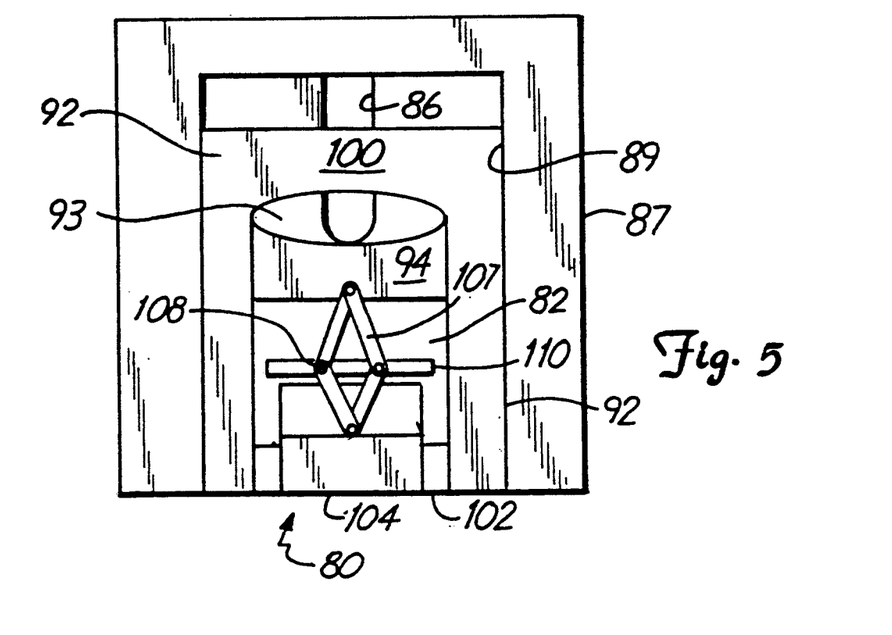

FIGS. 3-5 illustrate a preferred embodiment of the inflation apparatus of the present invention, the preferred embodiment differing from the embodiment shown and described in connection with FIGS. 1 and 2 by the orientation of the motor and the structure of the plunger operator. In other respects the two embodiments are the same, and like reference numerals designate like elements. Syringe 10 has its forward end connected to frame 70 in the same manner as syringe 10 was connected to frame 30 and cap 32 in FIG. 1. Frame 70 supports a pressure sensor arranged to bear against a diaphragm on syringe 10, the diaphragm being in fluid communication with chamber 26 of the syringe in the manner described and shown in FIG. 1. Connector 28 is mounted to the proximal end of tube 72 whose lumen 74 is in fluid communication with chamber 26 as previously described and in fluid communication with the lumen of the balloon catheter (not shown). The pressure sensor provides a signal output via leads 42, as described above.

Motor 76, which receives power through leads 60, is mounted to frame 70 near the forward end of syringe 10. Motor shaft 78 is connected to plunger operator for axially operating the plunger and changing the pressure of inflation fluid in chamber 26, as heretofore described.

Plunger operator 80 (FIG. 4) includes a first housing 82 having a first slot 84 for receiving plunger actuator 18 (FIG. 3) and a second slot 86 through which plunger 16 extends. Second housing 87 is fastened to first housing 82 and includes an opening 89 whose width is larger than the width of slot 84. A pair of internal slots 88 are positioned in the vertical legs of second housing 87 in opening 89 for receiving flanges 90 of a first slide mechanism 92. Slide mechanism 92 has an opening 93 at least as large as slot 84 to permit passage of plunger actuator 18 therethrough. A second slide mechanism 94 has a pair of flanges 96 arranged to be received in slots 98 in the opening formed in slide mechanism 92. Slide mechanism 94 and portion 100 on slide mechanism 92 are arranged to engage the end surface of actuator 18 (FIG. 3) when the actuator is in slot 84. Conveniently, housings 82 and 87 may be a single member, with slot 84 open through opening 89 to permit passage of plunger actuator 18. Housings 82 and 87 are shown separately in FIG. 4 for clarity. In either case, slide mechanisms 92 and 94 are arranged to slide within opening 89 to open and close opening 89 to permit release of plunger 16 of the syringe.

Spacers 102 connect button 104 to slide mechanism 92. Button 104 has a pair of flanges 105 that are engaged with engaging slots (not shown) in slot 106 of housing 82 to permit button 104 to reciprocate vertically (in FIG. 4) within slot 106.

Slide mechanisms 92 and 94 are arranged to reciprocate vertically (in FIG. 4) under the influence of button 104 to release plunger actuator 18 from operator 80. A scissors mechanism 107 (FIG. 5) is pivotally attached to button 104 and to slide mechanism 94 and includes pins 108 engaging slot 110 on housing 82. The arrangement is such that upward movement of button 104 (in FIGS. 4 and 5) carries slide mechanism 92 upwardly and pulls slide mechanism 94 downwardly to move the slide mechanisms to clear opening 93 to be free of plunger actuator 18. Thus, when button 104 is operated, the pressure on the piston attached to plunger 16 will react against the piston, causing the plunger to rapidly withdraw to relieve pressure within chamber 26 in barrel 12 without aid of motor 76. This feature provides a mechanical safety release of the plunger without reliance on the motor or motor actuator circuit.

Figure 6:
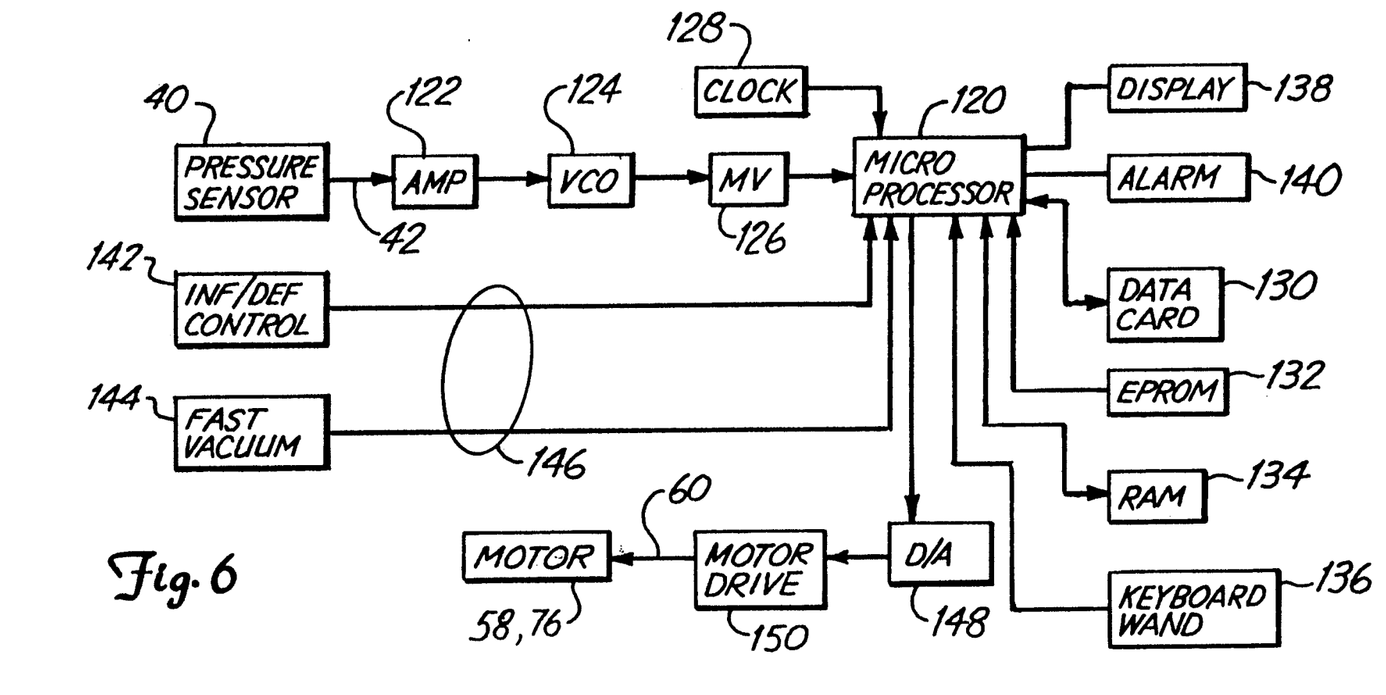
FIG. 6 is a block diagram of the control and display circuit for operating the inflation apparatus according to the present invention and for displaying information concerning the procedure.

FIG. 6 is a block circuit diagram of the apparatus for operating the inflation apparatus, and for displaying and recording pressure information. Microprocessor 120 receives digital signals representative of pressure from pressure sensor 40 via leads 42, amplifier 122, voltage-controlled oscillator (VCO) 124 and astable multivibrator 126. More particularly, pressure sensor 40 provides an analog signal which is amplified by amplifier 122, the analog signal being converted to an oscillating signal by VCO 124. The oscillating signal operates multivibrator 126 to provide pulses to microprocessor 120, the pulse rate being representative of fluid pressure within chamber 26 of syringe 10. Microprocessor 120 also receives a clock input from clock 128 as well as data from data card 130, electronically programmable read only memory (EPROM) 132 and random access memory (RAM) 134. Data card 130 may, for example, be a data card unique for each patient on which data is recorded concerning the patient and the patient's history, and onto which microprocessor 120 may record information concerning the PTCA procedure, including the type of catheter used. RAM 134 contains programs and data for use by the microprocessor during the performance of the procedure, and EPROM 132 contains other data and programs unique to the particular procedure. For example, EPROM 132 may contain data concerning the profile or diameter of plural dilatation balloons at various pressures. Keyboard or wand 136 may also be provided for inputting other data to microprocessor 120. For example, data concerning the specific dilatation balloon employed in the procedure may be input through keyboard 136 or by reading encoded stripes on the catheter via a wand.

Microprocessor 120 provides display output on display 138, and/or an alarm output at alarm 140. By way of example, pressure data, time of inflation, numbers of inflations, etc. may all be calculated and processed by microprocessor 120 through the use of pressure data from pressure sensor 40 and time data from clock 128, or prerecorded information from data card 130, EPROM 132 and/or RAM 134. Thresholds for inflation parameters may be preselected or may be calculated using prerecorded algorithms. It is known that dilatation balloons exhibit specific diameters at specific pressures. EPROM 132 may contain a look-up table or an algorithm to permit microprocessor 120 to calculate balloon diameter correlating to current pressure data for the identified balloon to permit display of information relating to balloon diameter on display 138 for use by the cardiologist.

Microprocessor 120 also receives input from inflation/deflation control 142 and fast vacuum control 144. Inflation/deflation control 142 may, for example, comprise a rocker switch for inflating the dilatation balloon (in one position) or deflating it (in the opposite position) or it may comprise a slide switch for fast and slow rate of inflation and deflation. A simple rocker or slide switch controls the rate of change pressure. Alternatively, control 142 may provide a digital signal representative of a desired pressure to direct the microprocessor to operate the motor to inflate or deflate the balloon to a specific pressure, selected by control 142, and measured by the pressure sensor. It is preferred that a fast vacuum control switch 144 also be employed to operate the motor to rapidly deflate the dilatation balloon and apply a vacuum to the syringe.

Controls 142 and 144 are connected by cable 146 to microprocessor 120. Microprocessor 120 provides an output via digital-to-analog (D/A) converter 148, motor drive circuit 150 to motor 58,76. Thus, motor 58,76 is operated under the control microprocessor 120. This permits the cardiologist to pre-program an inflation/deflation cycle or series of cycles, including pressure limits and limits on the number of inflations and the duration of inflation, as well as stepped inflation and/or deflation cycles.

In a simpler form of the invention, controls 42 and 144 may be connected by cable 146 directly to motor drive control 150, so the motor would not operate under the control of microprocessor 120. While direct connection of controls 142 and 144 to the motor drive control provides simpler control, control through the microprocessor permits greater versatility, including pre-programmed inflation/deflation cycles.

Figure 7:
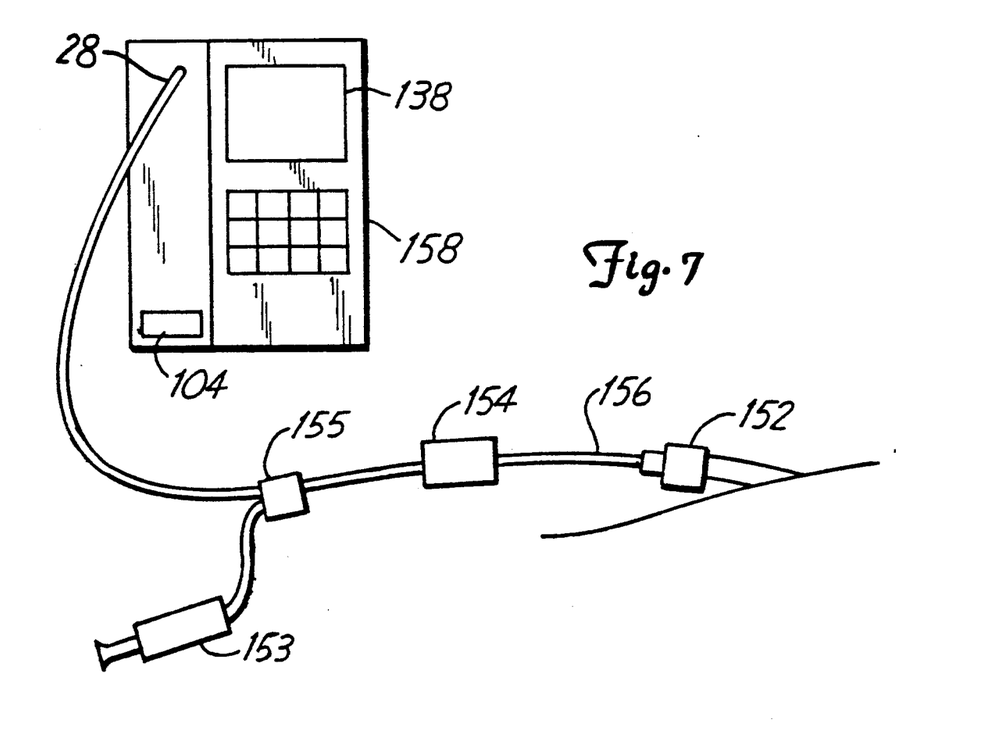
FIG. 7 is an illustration showing the use of the inflation apparatus according to the present invention in a PTCA procedure.

One feature of the present invention is illustrated in FIG. 7 in that the inflation apparatus may be operated with one hand. The cardiologist, without the assistance of a trained aide, may maintain the position of the catheter system 152 (which might comprise an introducer, guide catheter, dilatation catheter and guide wire) with one hand, and operate controls 142 and 144 on housing 154 with the other. Conveniently, housing 154 may be physically attached to tube 156 extending from connector 28 on syringe 10 to the manifold associated with catheter system 152. Microprocessor 120 may be mounted within housing 158 and connected via cable 146 (FIG. 6) embedded within tube 152 to housing 154 containing controls 142 and 144. Alternatively, housing 154 containing controls 142 and 144 may be separate from tube 156 and connected by a separated cable 146 to the microprocessor. Alternatively to the fixed wire connection of cable 146, controls 142 and 144 may be connected by a wireless link, such as infrared, ultrasonic, radio or magnetic modulated or pulse rate transmission to a receiver operatively associated with housing 158. In either case, display 138 is mounted in housing 158 for view by the cardiologist. Release button 104 is also mounted to housing 158 to release the plunger actuator and permit release of pressure from syringe 10 as heretofore described.

Another optional but desirable release mechanism is also illustrated in FIG. 7 wherein a hand-operated disposable syringe 153 is connected through Y-connector 155 to tube 156. Syringe 153 has a lock (not shown) to maintain the position of its piston and plunger at a forward end of the barrel when pressure is applied to the chamber of the syringe due to pressure in tube 156. In the event it is desired to release pressure in tube 156 (and hence, in the balloon catheter), the plunger of syringe 153 may be moved rearwardly to draw fluid into the syringe and create a vacuum in the balloon. Syringe 153 may also serve as a supply of inflation fluid to automatically load syringe 10 as described above.

Figure 8:
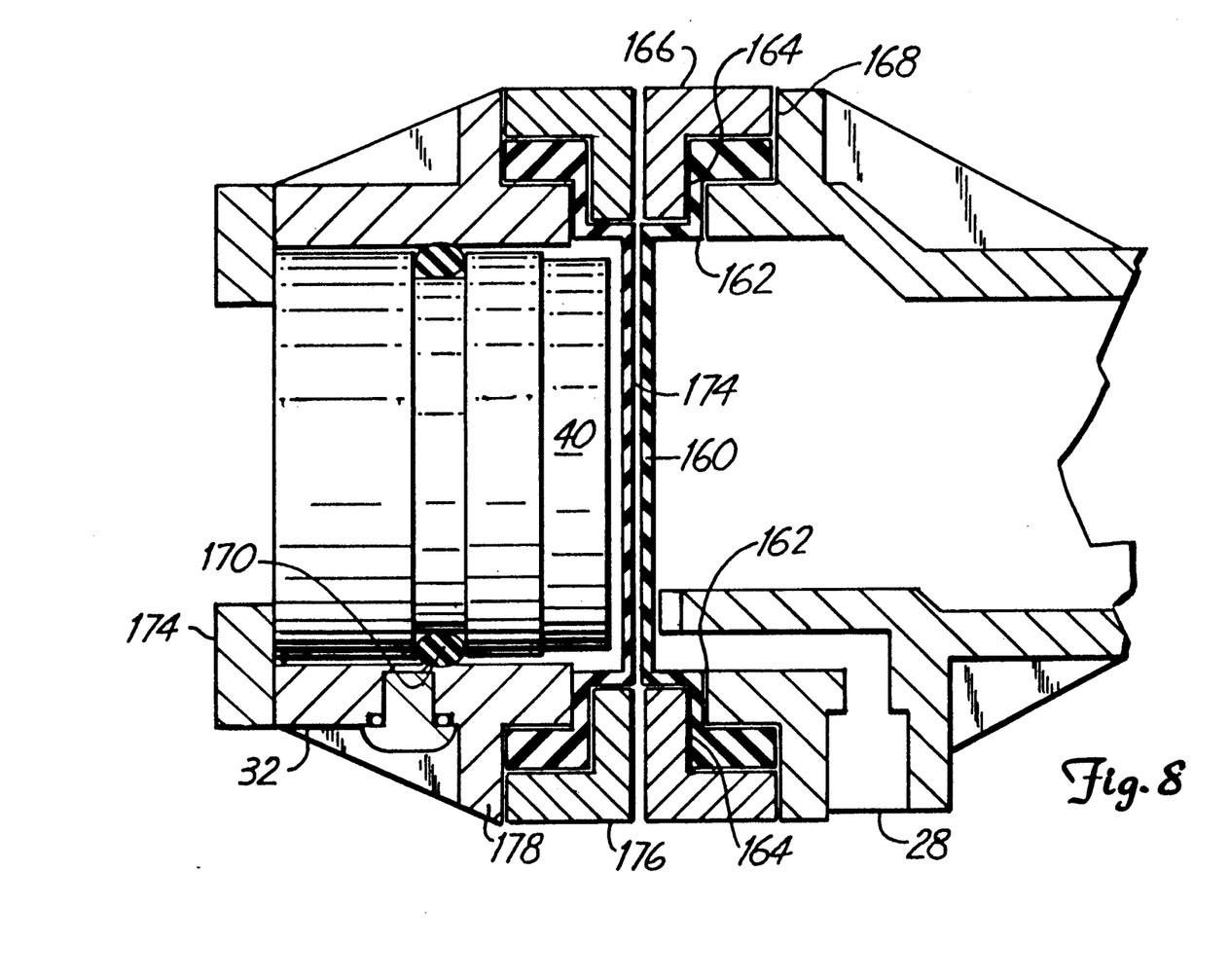
FIG. 8 is a section view of a portion of an inflation apparatus according to the present invention, illustrating an alternative arrangement of the diaphragm.

FIG. 8 illustrates a modified form of the diaphragm arrangement wherein syringe barrel 12 includes port 28 and a rubber diaphragm 160 sandwiched between shoulder 162 on barrel 12 and shoulder 164 on cap 166. Cap 166 is permanently attached to barrel 12, such as by adhesive bonding at annular interface 168. Cap 32 includes transducer 40 supported by O-ring 170 and retainer 172 in cap 32. Rubber diaphragm 174 is sandwiched between cap body 32 and closure 176, which are bonded together at interface 178.

Figure 9:
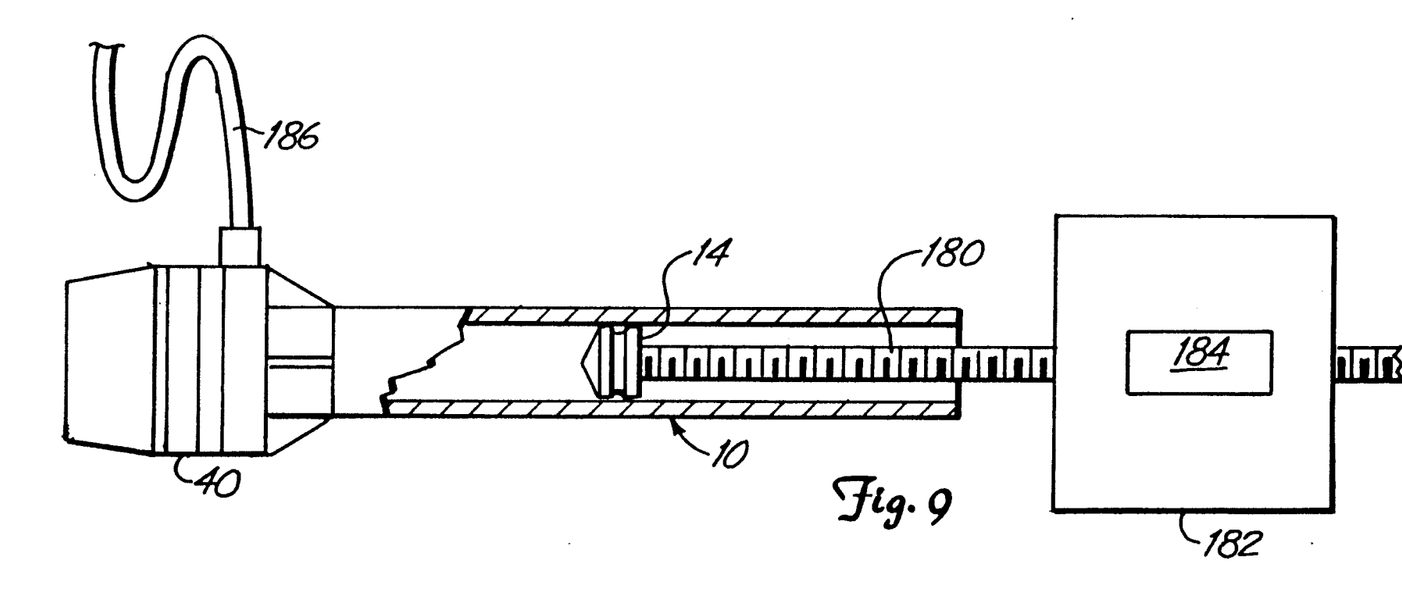
FIG. 9 is a side view, partly in cutaway cross-section, of an inflation apparatus according to another embodiment of the present invention.

FIG. 9 illustrates another embodiment of the invention wherein piston 14 of syringe 10 is attached directly to the shaft 180 of motor 182. Release mechanism 184 is mounted to motor 182 to release shaft 180, release mechanism 184 being manually operable by a button, like button 104. Preferably, release mechanism 184 includes bias means, such as a compression spring, to positively move shaft 180 to the right (as depicted in FIG. 9) to draw a vacuum within chamber 26, and hence within the balloon attached to the distal end of catheter 186. The embodiment of FIG. 9 illustrates two features. First, the emergency release releases the motor shaft rather than the motor (as in the embodiment of FIG. 1) or the plunger (as in the embodiment of FIGS. 3-5). Second, piston 14 is attached directly to the motor shaft, rather than attaching the plunger to the motor shaft. Thus, piston 14 may be fitted with a receptacle, such as a threaded receiver, to receive the end of motor shaft 180. The piston may be attached to and detached from the motor shaft for each use. The syringe and piston may be discarded after use.

The present invention thus provides an effective power-activated inflation apparatus which is easily and effectively operated with a single hand. The apparatus employs an inexpensive syringe which may be discarded after each procedure, the syringe being the principal portion of the inflation apparatus required to be sterile. Consequently, sterilization problems associated with prior motor-activated inflation devices are eliminated.

The diaphragm used in the disposable syringe described herein may be metal (such as stainless steel) or rubber or plastic. In any case it should exhibit adequate resiliency to transfer fluid pressure in the syringe chamber to the pressure sensor. Additionally, the diaphragm should provide a good fluid seal for the chamber.

Motor 58, 76 may be any suitable motor operated by a signal from motor drive circuit 150. As examples, the motor may be a stepper motor, linear motor or other motor capable of precision movement. The motor may include a gear drive or reduction assembly for added precision or to minimize resistance force on the motor due to pressure on the plunger. The motor must be capable of imparting force on piston 14 to produce pressures up to about 300 psi within chamber 26, and hence the dilatation balloon.

While pressure sensor 40 is shown mounted to the frame and part of the reusable assembly, the sensor may conveniently be mounted within the disposable syringe (such as to piston 14) and connected through a connector (such as mounted in the plunger operator) to the operating circuit. Alternatively, the syringe may be provided with an additional port and fluid connector for manual connection to the pressure sensor at the start of the procedure. While these alternative arrangements for the sensor provide more positive association of the sensor and the pressure within the syringe chamber, they also require that the sensor be disposed or sterilized after each use, thereby adding to the overall cost of the procedure.

Although the present invention has been described with reference to preferred embodiments, workers skilled in the will recognize that changes may be made in form and detail without departing from the spirit and scope of the invention.

What is claimed is:

1. Inflation apparatus for inflating a dilatation balloon in fluid communication with the lumen of a catheter, the inflation apparatus comprising:

a syringe having a longitudinal axis, a barrel having opposite ends and forming a chamber for containing an inflation fluid, a piston within the chamber, a fluid port in fluid communication with the chamber for connection to the lumen of the catheter, a plunger rod connected to the piston and extending through an end of the barrel and a plunger actuator connected to the end of the plunger rod extending through the end of the barrel, the apparatus further including a plunger operator connected to the drive rod, the plunger operator having second receiver supporting the plunger actuator;

a frame having a first receiver removably supporting an end of the barrel such that the longitudinal axis of the syringe has a fixed position relative to the frame;

a motor supported by the frame;

a drive rod operatively connected to the motor and supporting the piston, the motor being operable to move the piston such that the piston moves along the longitudinal axis under influence of the motor to change fluid pressure within the chamber;

control means for selectively operating the motor; and release means for releasing the piston from the influence of the motor without altering the fixed position of the longitudinal axis relative to the frame, the release means being supported by the plunger operator and so disposed and arranged to disconnect the plunger actuator from the second receiver.

2. Inflation apparatus according to claim 1 wherein the release means includes a mechanical latch having a closed position in which the plunger actuator is retained in the second receiver and an open position in which the plunger actuator is axially released from the second receiver, and manually operable means operating the latch between its closed and open positions.

3. Inflation apparatus according to claim 1 wherein the control means includes first means for operating the motor to move the piston at a first rate, and second means for operating the motor to move the piston to rapidly reduce fluid pressure in the chamber.

4. Inflation apparatus according to claim 1 further including sensor means supported by the frame and so disposed and arranged as to be operatively connected to the chamber to provide a data signal representative of fluid pressure within the chamber.

5. Inflation apparatus according to claim 4 further including display means responsive to the data signal for displaying information.

6. Inflation apparatus according to claim 5 wherein the display means includes a clock providing a clock signal, a processor connected to the sensor means and clock for processing the data signal and the clock signal to derive information concerning pressure within the chamber and duration of inflation, and a display device connected to the processor for displaying the information derived by the processor.

7. Inflation apparatus for inflating a dilatation balloon in fluid communication with the lumen of a catheter, the inflation apparatus comprising:
   a syringe having a longitudinal axis, a barrel having opposite ends and forming a chamber for containing an inflation fluid, a piston within the chamber, and a fluid port in fluid communication with the chamber for connection to the lumen of the catheter;
   a frame having a first receiver removably supporting an end of the barrel such that the longitudinal axis of the syringe has a fixed position relative to the frame;
   a motor supported by the frame;
   a drive rod operatively connected to the motor and supporting the piston, the motor being operable to move the piston such that the piston moves along the longitudinal axis under influence of the motor to change fluid pressure within the chamber;
   control means for selectively operating the motor, the control means including first means for operating the motor to move the piston at a first rate, and second means for operating the motor to move the piston to rapidly reduce fluid pressure in the chamber, the control means being operatively connected to the motor by wireless transmission; and
   release means for releasing the piston from the influence of the motor without altering the fixed position of the longitudinal axis relative to the frame.

8. Inflation apparatus for inflating a dilatation balloon in fluid communication with the lumen of a catheter, the inflation apparatus comprising:
   a syringe having a longitudinal axis, a barrel having opposite ends and forming a chamber for containing an inflation fluid, a piston within the chamber, and a fluid port in fluid communication with the chamber for connection to the lumen of the catheter;
   a frame having a first receiver removably supporting an end of the barrel such that the longitudinal axis of the syringe has a fixed position relative to the frame;
   a motor supported by the frame;
   a drive rod operatively connected to the motor and supporting the piston, the motor being operable to move the piston such that the piston moves along the longitudinal axis under influence of the motor to change fluid pressure within the chamber;
   control means for selectively operating the motor;
   release means for releasing the piston from the influence of the motor without altering the fixed position of the longitudinal axis relative to the frame;
   sensor means supported by the frame and so disposed and arranged as to be operatively connected to the chamber to provide a data signal representative of fluid pressure within the chamber; and
   display means responsive to the data signal for displaying information, the display means including a clock providing a clock signal, a processor connected to the sensor means and clock for processing the data signal and the clock signal to derive information concerning pressure within the chamber and duration of inflation, and a display device connected to the processor for displaying the information derived by the processor, the processor including a memory having a look-up table containing relational data relating the diameter of a dilatation balloon to pressure within the respective balloon for a plurality of dilatation balloons, the processor having input means for receiving data identifying the dilatation balloon in fluid communication with the catheter connected to the chamber, the processor being responsive to the dilatation balloon identification data and the data signal derived by the sensor means to select diameter information from the look-up table, the display device being responsive to the processor to display diameter information.

9. Inflation apparatus for inflating a dilatation balloon in fluid communication with the lumen of a catheter, the inflation apparatus comprising:
   a syringe having a longitudinal axis, a barrel having opposite ends and forming a chamber for containing an inflation fluid, a piston within the chamber, and a fluid port in fluid communication with the chamber for connection to the lumen of the catheter;
   a frame having a first receiver removably supporting an end of the barrel such that the longitudinal axis of the syringe has a fixed position relative to the frame;
   a motor supported by the frame;
   a drive rod operatively connected to the motor and supporting the piston, the motor being operable to move the piston such that the piston moves along the longitudinal axis under influence of the motor to change fluid pressure within the chamber;
   control means for selectively operating the motor;
   release means for releasing the piston from the influence of the motor without altering the fixed position of the longitudinal axis relative to the frame; and
   sensor means supported by the frame and so disposed and arranged as to be operatively connected to the chamber to provide a data signal representative of fluid pressure within the chamber, the sensor means including a pressure sensor for producing a signal having a magnitude representative of fluid pressure within the barrel, an oscillator responsive to the magnitude of the signal from the pressure sensor to provide a signal having a frequency representative of fluid pressure within the barrel, and a multivibrator responsive to the oscillator to provide a pulse signal having a repetition rate representative of the frequency of the signal provided by the oscillator.

10. Inflation apparatus for inflating a dilatation balloon in fluid communication with the lumen of a catheter, the inflation apparatus comprising:

a syringe having a longitudinal axis, a barrel having opposite ends and forming a chamber for containing an inflation fluid, a piston within the chamber, and a fluid port in fluid communication with the chamber for connection to the lumen of the catheter;

a frame having a first receiver removably supporting an end of the barrel such that the longitudinal axis of the syringe has a fixed position relative to the frame;

a motor supported by the frame;

a drive rod operatively connected to the motor and supporting the piston, the motor being operable to move the piston such that the piston moves along the longitudinal axis under influence of the motor to change fluid pressure within the chamber;

control means for selectively operating the motor;

release means for releasing the piston from the influence of the motor without altering the fixed position of the longitudinal axis relative to the frame;

sensor means supported by the frame and so disposed and arranged as to be operatively connected to the chamber to provide a data signal representative of fluid pressure within the chamber; and a diaphragm closing an end of the barrel, the diaphragm being so disposed and arranged relative to the sensor means as to transfer fluid pressure within the chamber to the sensor means to permit measurement of pressure within the chamber.

11. Inflation apparatus according to claim 10 wherein the diaphragm closes the end of the barrel opposite the end through which the plunger rod extends.

12. A power operator for operating a syringe to inflate a dilatation balloon in fluid communication with the lumen of a catheter, wherein the syringe has a longitudinal axis, a barrel arranged to be in fluid communication with the lumen and a piston movable in the barrel to change fluid pressure in the barrel, the power operator comprising:

a frame having a first receiver for removably supporting an end of the barrel to fix the position of the longitudinal axis of the syringe position relative to the frame;

a motor supported by the frame;

a drive rod operatively connected to the motor, the drive rod having a second receiver for removably supporting the piston of a syringe, the motor being operable to move the drive rod relative to the frame to move the piston along the longitudinal axis under influence of the motor to change fluid pressure within the barrel supported by the first receiver; the piston being connected to a plunger, the second receiver including a plunger operator connected to the drive rod, the second receiver being arranged to support the plunger;

control means for selectively operating the motor; and release means for releasing the piston from the influence of the motor without altering the fixed position of the longitudinal axis relative to the frame, the release means being supported by the plunger operator and arranged to disconnect the plunger from the second receiver.

13. A power operator according to claim 12 wherein the release means includes a mechanical latch having a closed position in which the plunger actuator is retained in the second receiver and an open position in which the plunger actuator is axially released from the second receiver, and manually operable means operating the latch between its closed and open positions.

14. A power operator for operating a syringe to inflate a dilatation balloon in fluid communication with the lumen of a catheter, wherein the syringe has a longitudinal axis, a barrel arranged to be in fluid communication with the lumen and a piston movable in the barrel to change fluid pressure in the barrel, the power operator comprising:

a frame having a first receiver for removably supporting an end of the barrel to fix the position of the longitudinal axis of the syringe position relative to the frame;

a motor supported by the frame;

a drive rod operatively connected to the motor, the drive rod having a second receiver for removably supporting the piston of a syringe, the motor being operable to move the drive rod relative to the frame to move the piston along the longitudinal axis under influence of the motor to change fluid pressure within the barrel supported by the first receiver;

control means for selectively operating the motor, the control means including first means for operating the motor to move the piston at a first rate, and second means for operating the motor to move the piston to rapidly reduce fluid pressure in the chamber, the control means being operatively connected to the motor by wireless transmission; and release means for releasing the piston from the influence of the motor without altering the fixed position of the longitudinal axis relative to the frame.

15. A power operator for operating a syringe to inflate a dilatation balloon in fluid communication with the lumen of a catheter, wherein the syringe has a longitudinal axis, a barrel arranged to be in fluid communication with the lumen and a piston movable in the barrel to change fluid pressure in the barrel, the power operator comprising:

a frame having a first receiver for removably supporting an end of the barrel to fix the position of the longitudinal axis of the syringe position relative to the frame;

a motor supported by the frame;

a drive rod operatively connected to the motor, the drive rod having a second receiver for removably supporting the piston of a syringe, the motor being operable to move the drive rod relative to the frame to move the piston along the longitudinal axis under influence of the motor to change fluid pressure within the barrel supported by the first receiver;

control means for selectively operating the motor;

release means for releasing the piston from the influence of the motor without altering the fixed position of the longitudinal axis relative to the frame;

sensor means supported by the frame and so disposed and arranged as to be operatively connected to a barrel which may be supported by the first receiver to provide a data signal representative of fluid pressure within the barrel; and display means responsive to the data signal for displaying information, the display means including a clock providing a clock signal, a processor connected to the sensor means and clock for processing the data signal and the clock signal to derive information concerning pressure within the chamber and duration of inflation, and a display device connected to the processor for displaying the information derived by the processor, the processor including a memory having a look-up table containing relational data relating the diameter of a dilatation balloon to pressure within the respective balloon for a plurality of dilatation balloons, the processor having input means for receiving data identifying the dilatation balloon in fluid communication with the catheter connected to the chamber, the processor being responsive to the dilatation balloon identification data and the data signal derived by the sensor means to select diameter information from the look-up table, the display device being responsive to the processor to display diameter information.

16. Power operator according to claim 15 further including a diaphragm closing an end of the barrel, the diaphragm being so disposed and arranged relative to the sensor means as to transfer fluid pressure to the chamber within the sensor means to permit measurement of pressure within the chamber.

17. Power operator according to claim 16 wherein the diaphragm closes the end of the barrel opposite the end through which the plunger rod extends.

18. A power operator for operating a syringe to inflate a dilatation balloon in fluid communication with the lumen of a catheter, wherein the syringe has a longitudinal axis, a barrel arranged to be in fluid communication with the lumen and a piston movable in the barrel to change fluid pressure in the barrel, the power operator comprising:

a frame having a first receiver for removably supporting an end of the barrel to fix the position of the longitudinal axis of the syringe position relative to the frame;

a motor supported by the frame;

a drive rod operatively connected to the motor, the drive rod having a second receiver for removably supporting the piston of a syringe, the motor being operable to move the drive rod relative to the frame to move the piston along the longitudinal axis under influence of the motor to change fluid pressure within the barrel supported by the first receiver;

control means for selectively operating the motor;

release means for releasing the piston from the influence of the motor without altering the fixed position of the longitudinal axis relative to the frame; and sensor means supported by the frame and so disposed and arranged as to be operatively connected to a barrel which may be supported by the first receiver to provide a data signal representative of fluid pressure within the barrel, the sensor means including a pressure sensor for producing a signal having a magnitude representative of fluid pressure within the barrel, an oscillator responsive to the magnitude of the signal from the pressure sensor to provide a signal having a frequency representative of fluid pressure within the barrel, and a multivibrator responsive to the oscillator to provide a pulse signal having a repetition rate representative of the frequency of the signal provided by the oscillator.

19. Power operator according to claim 18 further including a diaphragm closing an end of the barrel, the diaphragm being so disposed and arranged relative to the sensor means as to transfer fluid pressure within the chamber to the sensor means to permit measurement of pressure within the chamber.

20. Power operator according to claim 19 wherein the diaphragm closes the end of the barrel opposite the end through which the plunger rod extends.

21. A disposable syringe for use with a power operator for inflating a dilatation balloon of a catheter during a percutaneous transluminal angioplasty procedure wherein the power operator has a pressure sensor, the catheter having a lumen in fluid communication with the dilatation balloon, the syringe comprising:

a barrel having opposite ends and forming a chamber for containing an inflation fluid, one end of the barrel being so sized and arranged as to be operatively supported in a first receiver of the power operator;

a diaphragm closing an end of the barrel, the diaphragm being so disposed and arranged relative to the pressure sensor when the barrel is operatively supported by the power operator as to transfer fluid pressure within the chamber to the pressure sensor to permit measurement of pressure within the chamber;

a piston within the chamber;

a connection connected relative to the piston and so sized and arranged as to be operatively supported by a second receiver of the power operator to move the piston within the chamber to change fluid pressure in the chamber; and a fluid port in fluid communication with the chamber for connection to the lumen of the catheter.

22. The disposable syringe according to claim 21 wherein the piston includes means for connection to the drive rod of a motor.

23. The disposable syringe according to claim 21 further including a plunger rod having a first end connected to the piston and a second end extending through an end of the barrel, and the connection comprises a plunger actuator connected to the second end of the plunger rod, the plunger actuator being so sized and arranged relative to the second receiver as to be supportable thereby.

* * * * *

UNITED STATES PATENT AND TRADEMARK OFFICE
CERTIFICATE OF CORRECTION

PATENT NO. : 5,273,537

DATED : December 28, 1993

INVENTOR(S) : D. J. Haskvitz, et al

It is certified that error appears in the above-identified patent and that said Letters Patent is hereby corrected as shown below:

Col. 3, line 57, after "plunger", delete --1b--

Col. 5, line 15, before "engaging slot", insert --that are engaged with--

Col. 6, line 35, delete "controls 42", insert --controls --142--

Col. 8, line 19, after "in the", insert --art--

Signed and Sealed this

Fourteenth Day of June, 1994

Attest:

BRUCE LEHMAN

*Attesting Officer*         *Commissioner of Patents and Trademarks*